US012251419B2

(12) United States Patent
Kim et al.

(10) Patent No.: US 12,251,419 B2
(45) Date of Patent: Mar. 18, 2025

(54) SUSTAINED-RELEASE MICROPARTICLES CONTAINING DESLORELIN, AND PREPARATION METHOD THEREFOR

(71) Applicant: INVENTAGE LAB INC., Seongnam-si (KR)

(72) Inventors: Ju Hee Kim, Seongnam-si (KR); Se Yeon Kim, Suwon-si (KR)

(73) Assignee: INVENTAGE LAB INC., Seongnam-si (KR)

(*) Notice: Subject to any disclaimer, the term of this patent is extended or adjusted under 35 U.S.C. 154(b) by 729 days.

(21) Appl. No.: 17/605,185

(22) PCT Filed: Jan. 14, 2020

(86) PCT No.: PCT/KR2020/000657
§ 371 (c)(1),
(2) Date: Oct. 20, 2021

(87) PCT Pub. No.: WO2020/222399
PCT Pub. Date: Nov. 5, 2020

(65) Prior Publication Data

US 2022/0202894 A1 Jun. 30, 2022

(30) Foreign Application Priority Data

Apr. 30, 2019 (KR) ........................ 10-2019-0050437

(51) Int. Cl.

| | |
|---|---|
| ***A61K 38/09*** | (2006.01) |
| ***A61K 9/00*** | (2006.01) |
| ***A61K 9/113*** | (2006.01) |
| ***A61K 47/32*** | (2006.01) |
| ***A61K 47/34*** | (2017.01) |

(52) U.S. Cl.
CPC ............ *A61K 38/09* (2013.01); *A61K 9/0024* (2013.01); *A61K 9/113* (2013.01); *A61K 47/32* (2013.01); *A61K 47/34* (2013.01)

(58) Field of Classification Search
CPC ...... A61K 38/09; A61K 9/0024; A61K 9/113; A61K 47/32; A61K 47/34
See application file for complete search history.

(56) References Cited

U.S. PATENT DOCUMENTS

| | | | |
|---|---|---|---|
| 2002/0052320 | A1 | 5/2002 | Trigg et al. |
| 2008/0299168 | A1 | 12/2008 | Dadey |
| 2017/0252546 | A1 | 9/2017 | Park et al. |

FOREIGN PATENT DOCUMENTS

| | | | | |
|---|---|---|---|---|
| EP | 3586828 | * | 1/2020 | |
| EP | 3586828 | A1 * | 1/2020 | ............. A61K 31/00 |
| JP | 10045625 | A | 2/1998 | |
| JP | H1045625 | A | 2/1998 | |
| JP | 2004237177 | A | 8/2004 | |
| KR | 20120052355 | A | 5/2012 | |
| KR | 101583351 | B1 | 1/2016 | |
| WO | WO2007084460 | A2 | 7/2007 | |

OTHER PUBLICATIONS

Koji Kinoshita et al, From Single Microparticles to Microfluidic Emulsification: Fundamental Properties (Solubility, Density, Phase Separation) from Micropipette Manipulation of Solvent, Drug and Polymer Microspheres, Processes, 2016, vol. 4, Issue 49, pp. 1-28, MDPI, Basel, Switzerland.
International Search Report of PCT/KR2020/000657, May 1, 2020, English transaltion.
Koji Kinoshita et al, From Single Microparticles to Microfluidic Emulsification: Fundamental Properties (Solubility, Density, Phase Separation) from Micropipette Manipulation of Solvent, Drug and Polymer Microspheres, Processes , 2016, vol. 4, Thesis No. 49, pp. 1-28, MDPI, Basel, Switzerland.
R. Thun et al, Castration in Male Pigs: Techniques and Animal Welfare Issues, Journal of Physiology and Pharmacology, 2006, vol. 57, pp. 189-194, Polish Physiological Society, Kraków, Poland.
The extended European search report of EP 20 79 9171, Dec. 16, 2022.

* cited by examiner

*Primary Examiner* — Shirley V Gembeh
(74) *Attorney, Agent, or Firm* — STIP Law Group, LLC

(57) ABSTRACT

According to sustained-release microparticles containing deslorelin, and a preparation method therefor, of the present invention, sustained-release microparticles containing deslorelin in a formulation for subcutaneous administration are provided so that pain can be relieved during administration to animals, and a chemical castration effect can last for 2 to 36 months. In addition, the present invention is effective as a chemical castration agent for 2 to 8 months so as to have an excellent of removing boar taint.

10 Claims, 1 Drawing Sheet

[FIG. 1]
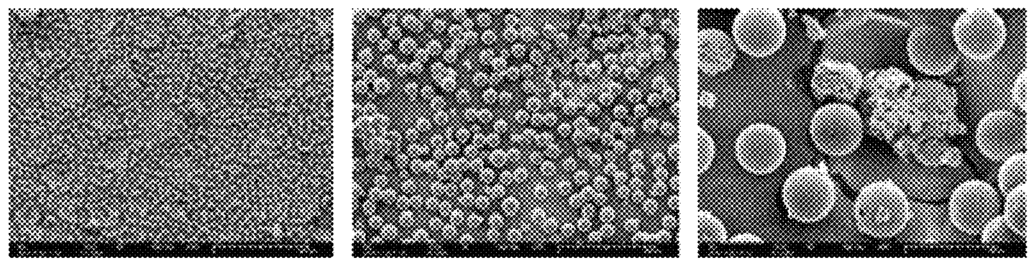
[FIG. 2]
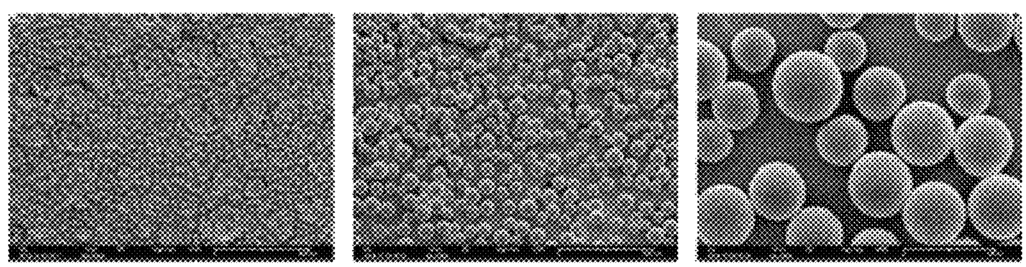

SUSTAINED-RELEASE MICROPARTICLES CONTAINING DESLORELIN, AND PREPARATION METHOD THEREFOR

CROSS-REFERENCE TO RELATED APPLICATIONS

This application is the U.S. National Phase under 35 U.S.C. § 371 of International Application No. PCT/KR2020/000657 filed on Jan. 14, 2020, which in turn claims the benefit of Korean Application No. 10-2019-0050437 filed on Apr. 30, 2019, the disclosures of which are incorporated by reference into the present application.

TECHNICAL FIELD

The present disclosure relates to sustained-release microparticles containing deslorelin and a preparation method therefor, and more specifically, to sustained-release microparticles containing deslorelin capable of maintaining a chemical castration effect by continuously releasing the deslorelin for a long time when injected into the body of an animal, and a preparation method therefor.

BACKGROUND ART

Orchiectomy (removal of testicles) or castration of male ruminants is necessary for a number of reasons, primarily to reduce aggression, reduce the risk of harm to humans and other animals, and facilitate handling.

In addition, the orchiectomy (removal of testicles) or castration, in more dedicated breeding for weight gain, is necessary to avoid the risk of unwanted hybridization by genetically low potential males, or to provide a better quality of carcass due to increasing the ratio of best meat quality and accumulating fat compared to whole animals.

Castration methods include surgical procedures, such as a cutting method, a spermatic cord attachment method, a torsion method, a scrotum attachment method, a extrusion method, partial castration, bloodless castration, etc., and in addition, include a method of irradiating more than a certain amount of radiation sensitive to the gonads to lose gonadal ability.

However, physical castration of animals is a problem in terms of animal welfare because it causes very serious pain and stress in animals, and was decided to be banned in about 2009 in European countries such as Switzerland, Norway, Belgium and the Netherlands, and similar measures are being considered in Korea (Thun R et al., Castration in male pigs: Techniques and animal welfare issues. Journal of Physiology and Pharmacology, 57, pp. 189-194, 2006).

Another suitable method for carrying out infertility and removal of libido is a chemical method. In the 1960s, a study was initiated to use a sclerotic substance directly injected into testis or spermatic cord for the purpose of promoting the overall loss of a function of the testis or spermatic cord (producing sperm and androgen hormone).

Chemical infertilization has been attempted in monkeys, hamsters, rabbits, rats and dogs by intratesticular administration of several agents as follows: ferrous chloride (Kar et al. 1965), danazole (Dixit et al., 1975), BCG (Das et al. 1982), tannin zinc (Fahim et al., 1982), glycerol (Weinbauer et al., 1985, Immegart 2000), glucose, NaCl (Heath et al., 1987, Russell et al. 1987), DBCP (Shemi et al. 1988), lactic acid (Fordyce et al. 1989), zinc arginine (Fahim et al. 1993), sodium fluoride (Sprando et al. 1996), formalin (Balar et al. 2002) and calcium chloride (Samanta 1998, Jana et al. 2002), potassium glacial permanganate (Giri et al. 2002). In ruminants, a method injecting lactic acid (Hill et al. 1985), tannic acid, zinc sulfate (Feher et al. 1985), alpha hydroxypropionic acid (Cohen et al. 1995), formalin (Ijaz et al. 2000) CastrateQuin 14 (Soerensen et al. al. 2001) into the male testis was used.

Recently, deslorelin, which is a synthetic analogue of gonadotropin-releasing hormone (GnRH), was used in the treatment of chemical castration in male animals and benign prostatic hyperplasia in dogs.

However, there is a problem in that since the deslorelin is injected into the body of the animal in the form of an implant, a severe pain is caused to the animal during administration.

Therefore, in the case of using deslorelin as a chemical castration agent, there is a need to develop a product that can maintain the effect as an agent for temporary infertility for a long time without causing severe pain to animals.

PRIOR ART DOCUMENTS

Patent Documents (Patent Document 1) KR 10-2012-0052355 A1

DISCLOSURE

Technical Problem

An object of the present disclosure is to provide sustained-release microparticles containing deslorelin, and a preparation method therefor.

Another object of the present disclosure is to provide sustained-release microparticles containing deslorelin in a subcutaneous injection formulation to provide sustained-release microparticles containing deslorelin capable of maintaining the effect as a chemical castration agent of male animals for a long time, and a preparation method therefor.

Still another object of the present disclosure is to provide sustained-release microparticles containing deslorelin, which is effective as a chemical castration agent for 2 to 8 months and has an excellent effect of removing boar taint in male pigs, when the sustained-release microparticles containing deslorelin are administered in a subcutaneous injection formulation, and a preparation method therefor.

Another object of the present invention is to provide sustained-release microparticles having a uniform diameter to provide a method for preparing sustained-release microparticles capable of alleviating pain and maintaining a chemical castration effect for 2 to 36 months when administered to an animal, and sustained-release microparticles prepared by the method.

Technical Solution

To achieve the above objects, a method for preparing sustained-release microparticles containing deslorelin according to an embodiment of the present disclosure includes steps of: 1) preparing a first mixture by mixing an active pharmaceutical ingredient (API) mixture in which deslorelin is dissolved in a first solvent and a biodegradable polymer mixture in which a biodegradable polymer is dissolved in a second solvent; 2) dissolving a surfactant in water to prepare a second mixture; 3) injecting the first mixture of the step 1) into a channel in a linear direction and allowing the first mixture to flow therein; 4) injecting the second mixture of the step 2) into a channel formed on either side or one side so as to form a cross-point with the channel in which the first mixture of the step 3) flows in the linear direction and allowing the second mixture to flow therein, and then crossing the flow in the linear direction with the flow in a lateral direction to prepare microparticles in which deslorelin is evenly distributed; 5) collecting the microparticles generated at the cross-point of the step 4); 6) removing an organic solvent present on the surface of the microparticles collected in the step 5); and 7) washing and drying the microparticles of the step 6), wherein the prepared microparticles are an $O_1$ (Oil)/$O_2$ (Oil)/W (Water) emulsion or a $W_1$ (Water)/O (Oil)/$W_2$ (Water) emulsion, and have an average diameter of 25 to 140 μm The microparticles may contain the deslorelin and the biodegradable polymer at a weight ratio of 1:4 to 1:30.

The API mixture may be mixed with deslorelin and the first solvent at a weight ratio of 1:3 to 1:8.

The biodegradable polymer mixture may be mixed with the biodegradable polymer and the second solvent at a weight ratio of 1:10 to 3:10.

The first mixture may be mixed with the API mixture and the biodegradable polymer mixture at a weight ratio of 1:4 to 1:20.

The second mixture may further include an osmotic pressure regulator.

The solvent may be selected from the group consisting of methanol, chloroform, chloromethane, dichloromethane, trichloroethane, water, ethanol, dimethylsulfoxide, and a mixture thereof.

The biodegradable polymer may be selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof.

The ratio of a width (w) of the cross section of the channel to the average diameter (d') of the microparticles is the range of 0.7 to 1.3.

The ratio of a depth (d) of the cross section of the channel to the average diameter (d') of the microparticles is in the range of 0.7 to 1.3.

The sustained-release microparticles containing deslorelin according to another embodiment of the present disclosure are prepared using the preparation method described above.

The composition for subcutaneous injection comprising sustained-release microparticles containing deslorelin according to another embodiment of the present disclosure may contain sustained-release microparticles and a suspension solvent.

The injection formulation for removing boar taint in male pigs and containing deslorelin according to another embodiment of the present disclosure, contains sustained-release microparticles and a suspension solvent, wherein the formulation is for removing boar taint in male pigs and is provided by subcutaneous or intramuscular injection, and the deslorelin may be released continuously for 2 to 8 months.

The injection formulation for a chemical castration agent of male animals containing deslorelin according to another embodiment of the present disclosure, contains sustained-release microparticles and a suspension solvent, wherein the formulation is for chemical castration of male animals and is provided by subcutaneous or intramuscular injection, and the deslorelin may be released continuously for 2 to 36 months.

Hereinafter, the present invention will be described in more detail.

The method for preparing sustained-release microparticles containing deslorelin according to an embodiment of the present disclosure includes steps of: 1) preparing a first mixture by mixing an active pharmaceutical ingredient (API) mixture in which deslorelin is dissolved in a first solvent and a biodegradable polymer mixture in which a biodegradable polymer is dissolved in a second solvent; 2) dissolving a surfactant in water to prepare a second mixture; 3) injecting the first mixture of the step 1) into a channel in a linear direction and allowing the first mixture to flow therein; 4) injecting the second mixture of the step 2) into a channel formed on either side or one side so as to form a cross-point with the channel in which the first mixture of the step 3) flows in the linear direction and allowing the second mixture to flow therein, and then crossing the flow in the linear direction with the flow in a lateral direction to prepare microparticles in which deslorelin is evenly distributed; 5) collecting the microparticles generated at the cross-point of the step 4); 6) removing an organic solvent present on the surface of the microparticles collected in the step 5); and 7) washing and drying the microparticles of the step 6), wherein the prepared microparticles are $O_1$ (Oil)/$O_2$ (Oil)/W (Water) emulsion or $W_1$ (Water)/O (Oil)/$W_2$ (Water) emulsion, and have an average diameter of 25 to 140 μm.

The deslorelin is a synthetic analogue of naturally occurring gonadotropin-releasing hormone (GnRH), which is prepared using deslorelin acetate.

Unlike other GnRH agonists, which are mainly used to inhibit luteinizing hormone (LH) and follicle stimulating hormone (FSH) by ultimate down-regulation of the pituitary gland, the deslorelin is mainly used to increase an initial flare effect of the pituitary gland and an LH secretion associated therewith.

The deslorelin is used veterinarily to induce ovulation in mares as part of an artificial insemination process or to stabilize high-risk pregnancies in livestock. The deslorelin is also used for chemical castration in dogs and ferrets, and may also be used to treat benign prostatic hyperplasia in dogs.

The present disclosure relates to a method of preparing sustained-release microparticles, by adjusting the size of the microparticles so that the drug release effect may be maintained in the body of an animal for 2 to 36 months.

More specifically, the microparticles have a spherical shape, and are in uniformly mixed state of the biodegradable polymer and the deslorelin.

General sustained-release microparticles are composed of a drug-encapsulated form, but in the case of the present disclosure, are in uniformly mixed state of the biodegradable polymer and the deslorelin as a spherical particle, and the microparticles themselves are injected into the body of an animal, and the deslorelin is released as the biodegradable polymer is decomposed, resulting in a medicinal effect.

More specifically, a method of preparing sustained-release microparticles according to an embodiment of the present disclosure will be described in the following.

The step 1) is a step of preparing the first mixture, by mixing an active pharmaceutical ingredient (API) mixture in which the deslorelin is dissolved in the first solvent and a biodegradable polymer mixture in which the biodegradable polymer is dissolved in the second solvent.

The API mixture means that the deslorelin is uniformly mixed in the solvent by dissolving the deslorelin in the first solvent. The API mixture is mixed with the deslorelin and the first solvent at a weight ratio of 1:3 to 1:8. When preparing the API mixture within the range above, it is possible to prepare microparticles in which the biodegradable polymer and the deslorelin are uniformly mixed.

The biodegradable polymer mixture means that the biodegradable polymer is uniformly mixed in the solvent by dissolving the biodegradable polymer in the second solvent. The second solvent may be an organic solvent to completely dissolve the biodegradable polymer. The biodegradable polymer mixture is mixed with the biodegradable polymer and the second solvent at a weight ratio of 1:10 to 3:10. When preparing the biodegradable polymer mixture within the range above, it is possible to prepare microparticles in which the biodegradable polymer and the deslorelin are uniformly mixed.

In addition, the first mixture is mixed with the API mixture and the biodegradable polymer mixture at a weight ratio of 1:4 to 1:20. When preparing the API mixture within the range above, it is possible to prepare microparticles in which the biodegradable polymer and the deslorelin are uniformly mixed.

The biodegradable polymer is selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof, and preferably polylactide-co-glycolide (PLGA), but is not limited thereto.

In addition, the solvent may be one or more selected from the group consisting of methanol, chloroform, chloromethane, dichloromethane, trichloroethane, water, ethanol, dimethylsulfoxide, and a mixture thereof. Preferably, the first solvent is methanol or water, and the second solvent is dichloromethane, but is not limited thereto.

Depending to the type of first solvent, there are differences in the prepared microparticles as an $O_1$ (Oil)/$O_2$ (Oil)/W (Water) emulsion or an $W_1$ (Water)/O (Oil)/$W_2$ (Water) emulsion, wherein, if methanol is used as the first solvent, the microparticles are prepared in the form of an $O_1$ (Oil)/$O_2$ (Oil)/W (Water) emulsion, and if water is used as the first solvent, the microparticles are prepared in the form of an $W_1$ (Water)/O (Oil))/$W_2$ (Water) emulsion.

The $O_1$ (Oil)/$O_2$ (Oil)/W (Water) emulsion, or the $W_1$ (Water)/O (Oil)/$W_2$ (Water) emulsion, or both are prepared in a form in which the deslorelin is evenly distributed within the microparticles as final spherical microparticles as they proceed to a subsequent stirring process and a freeze-drying step.

The step 1) is a step of preparing a first mixture by mixing an API mixture in which deslorelin acetate is completely dissolved in methanol or water, and a biodegradable polymer mixture in which a biodegradable polymer is completely dissolved in dichloromethane. The first mixture contains the deslorelin and the biodegradable polymer at a weight ratio of 1:4 to 1:30. If the biodegradable polymer is contained below the above range, the weight ratio of the biodegradable polymer is small compared to the weight of deslorelin, and thus it may be difficult to prepare the microparticles of the form in which deslorelin is evenly distributed and contained in the spherical biodegradable polymer particles. If the biodegradable polymer is contained in excess of the above weight ratio, the content of deslorelin in the microparticles is small, and thus the duration of the drug effect may be shortened, or a large amount of microparticles may need to be administered in order to administer the drug at a desired concentration.

The step 2) is a step of preparing a second mixture by dissolving a surfactant in water. The surfactant may be used without limitation as long as the surfactant can help the biodegradable polymer solution form a stable emulsion. Specifically, the surfactant may be any one or more selected from the group consisting of nonionic surfactants, anionic surfactants, cationic surfactants, and a mixture thereof, and more specifically, one or more selected from the group consisting of methylcellulose, polyvinylpyrrolidone, lecithin, gelatin, polyvinyl alcohol, polyoxyethylene sorbitan fatty acid ester, polyoxyethylene castor oil derivative, sodium lauryl sulfate, sodium stearate, ester amine, linear diamine, fatty amine, and a mixture thereof, preferably polyvinyl alcohol, but is not limited thereto.

The second mixture may further contain an osmotic pressure regulator in consideration of physical properties of deslorelin acetate.

More specifically, the microparticles are formed as the first mixture and the second mixture intersect, and in this case, the deslorelin may be exited into the second mixture. In order to prevent this problem, an osmotic pressure regulator is further contained in the second mixture.

The osmotic pressure regulator is selected from the group consisting of mannitol, sodium chloride (NaCl), and a mixture thereof, preferably mannitol alone, or both mannitol and sodium chloride.

The osmotic pressure regulator may contain 1 to 10% by weight of mannitol, or 1 to 10% by weight of mannitol and 0.2 to 2.0% by weight of sodium chloride, based on the total weight of the second mixture. It is possible to prevent the deslorelin from being mixed into the second mixture and to prepare the form in which the deslorelin is uniformly distributed within the spherical microparticles, by mixing and using the osmotic pressure regulator within the range above.

The step 3) (S300) and the step 4) (S400) are steps of injecting the first mixture and the second mixture into microchannels formed on a wafer and allowing the first mixture and the second mixture to flow therein.

More specifically, aluminum is deposited on a silicon wafer using an e-beam evaporator, and a photoresist is patterned on the aluminum using a photolithography technique. Thereafter, aluminum is etched using the photoresist as a mask, the photoresist is removed, silicon is etched with deep ion reactive etching (DRIE) using aluminum as a mask, and then, glass is anodic bonded onto the wafer to be sealed, after the aluminum is removed, thereby preparing the microchannel.

Further, the microchannel has an average diameter of 40 to 100 μm, preferably 40 to 60 μm, and more preferably 50 μm, but the average diameter thereof is not limited thereto. If the average diameter of the microchannel is less than 40 μm, there is a possibility that the microparticles will be prepared as small microparticles having a diameter of 20 μm or less, so the microparticles are highly likely to being engulfed by macrophages after injection into the human body, thereby affecting the release of effective drugs and the absorption thereof in vivo. In addition, if the average diameter of the microchannel is larger than 100 μm, there is a possibility that the prepared microparticles will have a diameter of 150 μm or more, so foreign body sensation and pain may be increased when the injectable agent is administered, and the particle size distribution of the prepared particle may be increased, thereby making it difficult to prepare microparticles having a uniform particle size.

In addition, a width (w) and a depth (d) of a cross section of the microchannel are closely related to an average diameter (d') of the microparticles to be prepared. As shown in FIG. 8, the ratio of the width (w) of the cross section of the microchannel to the average diameter (d') of the microparticles is in the range of 0.7 to 1.3, and the ratio of the depth (d) of the cross section of the microchannel to the average diameter (d') of the microparticles is in the range of 0.7 to 1.3.

That is, once the average diameter (d') of the microparticles to be prepared is determined, it is possible to prepare microparticles having a desired size only when the ratio of the width (w) and depth (d) of the cross section of the microchannel to the d' is set in the range of 0.7 to 1.3.

The step 3) is a step of injecting the first mixture into a microchannel in a linear direction and allowing the first mixture to flow therein. The step 4) is a step of injecting the second mixture into a microchannel formed on either side or one side so as to form a cross-point with the microchannel in the linear direction and allowing the second mixture to flow therein.

That is, the first mixture flows along the channel in a linear direction, and the second mixture flows along a channel formed on either side or one side with respect to the channel in the linear direction and meets the flow of the first mixture.

At this time, when injected into the channel in a linear direction, the first mixture is injected under a constant pressure condition and allowed to flow at a constant flow rate, and at this time, the pressure condition is 200 to 2,000 mbar, preferably 1,100 mbar, but is not limited thereto.

Also, when injected into the microchannel in either side or one side, the second mixture is injected under a constant pressure condition and allowed to flow at a constant flow rate, and at this time, the pressure condition is 500 to 2,400 mbar, preferably 2,200 mbar, but is not limited thereto.

That is, in order to make the flow of the second mixture forming a cross-point with the flow of the first mixture faster than that of the first mixture injected into the channel in the linear direction, the second mixture is allowed to flow under a higher pressure condition.

As described above, by varying the flow rates of the first mixture and the second mixture, and making the flow rate of the second mixture faster than that of the first mixture, the second mixture having a relatively faster flow rate compresses the first mixture at the point where the flow of the first mixture meets the flow of the second mixture and at this time, due to the repulsive force of the first mixture and the second mixture, the biodegradable polymer and the deslorelin in the first mixture generate spherical microparticles, and more specifically, the microparticles in which the deslorelin is evenly distributed in the spherical biodegradable polymer, are formed.

The step 5) is a step of collecting microparticles, and the microparticles are collected in a water bath containing the second mixture, which is a mixed solution of surfactant and water, thereby preventing aggregation between the initially generated microparticles.

In the step 5), the second mixture prepared in the step 2), that is, a mixed solution of a surfactant and water may be used, or a mixed solution having a different content of the components of the second mixture may be used.

The second mixture prepared in the step 2) may contain 1 to 2% by weight of a surfactant and the remaining water, and may be used in the step 5) as it is, and in order to prevent more efficiently the aggregation between microparticles in the water bath in the step 5), a mixed solution of a surfactant using two types of surfactants, and water may be used.

When two types of surfactants are used as described above, 0.1 to 2% by weight of polyvinyl alcohol, 1 to 10% by weight of mannitol, and the remaining water, based on the weight of the total mixed solution, may be included.

When a mixed solution is prepared by including two types of surfactants as described above and used in the step 5), the of aggregation between microparticles may be efficiently prevented.

In the case of using the second mixture in the step 2) as it is, after being prepared in the step 2), a part is injected into the channel, and the other is moved to the water bath in the step 5), and the second mixture is used to prevent the aggregation between the collected microparticles.

The step is, after the step of collecting the microparticles, a step of stirring the microparticles collected in the water bath, the microparticles are stirred under a constant temperature condition and at a stirring speed to evaporate and remove the organic solvent present on the surface of the microparticles. At this time, the step of stirring microparticles is performed in the order of: a first stirring step under the stirring conditions of a speed of 200 to 600 rpm for 0.5 to 2 hours at 15 to 25° C.; after the first stirring step, a second stirring step under the stirring conditions of a speed of 200 to 800 rpm for 2 to 6 hours at 30 to 50° C.; and after the second stirring step, a third stirring step under the stirring conditions of a speed of 200 to 800 rpm for 0.5 to 1.5 hours at 15 to 25° C.

As the stirring process is performed by varying the stirring speed and temperature conditions for stirring the microparticles, the evaporation speed of the organic solvent present on the surface of the microparticles may be regulated. That is, by evaporating the organic solvent present on the surface of the microparticles through the stirring process, it is possible to remove the harmful solvent and prepare microparticles having a smooth surface.

The temperature at which the first mixture and the second mixture flow through the microchannel is also 15 to 20° C., preferably 17° C. That is, after flowing through the microchannel and forming the cross-point to generate microparticles, the first mixture and the second mixture are kept at a constant low temperature of 15 to 20° C. until the collected microparticles are subjected to the first stirring. It is possible to prepare and maintain spherical particles only when a low temperature is maintained during the preparing process of microparticles. That is, in the case of non-low temperature conditions, it is difficult to prepare particles having a constant spherical shape.

Finally, in the step of washing and drying the microparticles, the microparticles from which all the organic solvents on the surface are removed by stirring are washed several times with water to remove the surfactant remaining on the microparticles, and then freeze-dried.

The microparticles may be prepared by injecting a mixture into the channel formed on a wafer and allowing the mixture to flow therein. More specifically, the channel is a microchannel.

More specifically, aluminum is deposited on a silicon wafer using an e-beam evaporator, and a photoresist is patterned on the aluminum using a photolithography technique. Thereafter, aluminum is etched using a photoresist as a mask, the photoresist is removed, silicon is etched with deep ion reactive etching (DRIE) using aluminum as a mask, and then, glass is anodic bonded onto the wafer to be sealed, after the aluminum is removed, thereby preparing the microchannels.

The finally produced microparticles are an O (Oil)/O (Oil)/W (Water) emulsion, and are in a form in which the deslorelin drug is evenly distributed in spherical biodegradable polymer microparticles.

The microparticles have a particle diameter of 25 to 140 μm, and include the deslorelin and the biodegradable polymer at a weight ratio of 1:4 to 1:30. If the average diameter of the microparticles is less than 25 μm, the microparticles are highly likely to being engulfed by macrophages after injection into the animal body, thereby affecting the release of drugs from the microparticles and the absorption thereof in vivo. If the average diameter of the microparticles exceeds 140 μm, a thick gauge syringe needle is used to the animal to which the injectable agent is administered, thereby increasing pain during drug administration.

The weight ratio of the biodegradable polymer and the deslorelin contained in the microparticles is the same as that in the first mixture. Thus, the microparticles containing the biodegradable polymer and the deslorelin may be prepared at the same ratio as the weight ratio in the first mixture by preparing the microparticles and evaporating and removing all organic solvents.

In one embodiment of the present disclosure, it is intended to provide a composition for subcutaneous injection containing sustained-release microparticles containing deslorelin for removing boar taint in male pigs.

In the case of male pigs, a peculiar smell (boar taint) occurs, and the pigs should be castrated several months before slaughter, so that the meat does not smell and can be edible, but there are animal ethics aspects and difficulties of the actual castration process.

That is, in the case of physical castration, there are problems in the animal ethics aspects and difficulties of the actual castration process, so castration several months before slaughter has practically many difficulties.

The sustained-release microparticles of the present disclosure may exhibit a drug release effect in the body of an animal for 2 to 36 months by adjusting the size of the particles.

Accordingly, when the sustained-release microparticles of the present disclosure is used as a composition for a subcutaneous injection for removing boar taint in male pigs, the effect of releasing the deslorelin is maintained for 2 to 8 months in the body of male pigs, thereby improving the effect as a chemical castration agent.

Advantageous Effects

According to sustained-release microparticles containing deslorelin according to the present disclosure, and a preparation method therefor, sustained-release microparticles containing deslorelin in a formulation for subcutaneous administration are provided so that pain can be relieved during administration to animals, and a chemical castration effect can last for 2 to 36 months.

In addition, the sustained-release microparticles of the present disclosure are effective as a chemical castration agent for 2 to 8 months, and thus have excellent effect of removing boar taint in male pigs.

BRIEF DESCRIPTION OF DRAWINGS

FIG. 1 is an SEM photograph of particles for each of stirring conditions according to one embodiment of the present disclosure.

FIG. 2 is an SEM photograph of particles for each of stirring conditions according to an embodiment of the present disclosure.

BEST MODE

The present disclosure relates to a method for preparing sustained-release microparticles containing deslorelin, the method comprising steps of: 1) preparing a first mixture by mixing an active pharmaceutical ingredient (API) mixture in which deslorelin is dissolved in a first solvent and a biodegradable polymer mixture in which a biodegradable polymer is dissolved in a second solvent; 2) dissolving a surfactant in water to prepare a second mixture; 3) injecting the first mixture of the step 1) into a channel in a linear direction and allowing the first mixture to flow therein; 4) injecting the second mixture of the step 2) into a channel formed on either side or one side so as to form a cross-point with the channel in which the first mixture of the step 3) flows in the linear direction and allowing the second mixture to flow therein, and then crossing the flow in the linear direction with the flow in a lateral direction to prepare microparticles in which deslorelin is evenly distributed; 5) collecting the microparticles generated at the cross-point of the step 4); 6) removing an organic solvent present on the surface of the microparticles collected in the step 5); and 7) washing and drying the microparticles of the step 6), wherein the prepared microparticles are an $O_1$ (Oil)/$O_2$ (Oil)/W (Water) emulsion or a $W_1$ (Water)/O (Oil)/$W_2$ (Water) emulsion, and have an average diameter of 25 to 140 μm.

MODE FOR INVENTION

Hereinafter, embodiments of the present disclosure will be described in detail so that those skilled in the art to which the present disclosure pertains can easily carry out the present disclosure. However, the present disclosure may be embodied in a variety of different forms and is not limited to the embodiments described herein.

1. Preparation of Sustained-Release Microparticles

Example 1

Deslorelin acetate was dissolved in methanol to prepare an API mixture. Polylactide-co-glycolide (PLGA) was dissolved in dichloromethane to prepare a biodegradable polymer mixture.

The first mixture was prepared by mixing the API mixture and the biodegradable polymer mixture. At this time, the weight ratio of polylactide-co-glycolide and deslorelin acetate in the first mixture was 4:1.

As the polylactide-co-glycolide (PLGA 7502), a biodegradable polymer was used in which the molar ratio of a lactide and glycolide is 75/25.

Polyvinyl alcohol, which is a surfactant, was mixed with water to prepare the second mixture containing 0.25% by weight of polyvinyl alcohol.

The first mixture and the second mixture were injected into microchannels formed on a silicone wafer and allowed to flow therein. At this time, in order for the first mixture and the second mixture to flow at a constant flow rate, the first mixture was allowed to flow under a pressure condition of 800 mbar, and the second mixture was allowed to flow under a pressure condition of 1400 mbar. The temperature condition was maintained at 17° C.

The microparticles generated at the cross-point where the flow of the first mixture meets the flow of the second mixture were collected in a water bath containing the second mixture. The microparticles collected in the water bath was firstly stirred at 17° C. for 1 hour at a speed of 400 rpm, and then was secondly stirred for 3 hours at a speed of 600 rpm with the temperature raised to 40° C., and was thirdly stirred at a speed of 600 rpm for 1 hour with the temperature lowered to 25° C.

After the stirring was completed, the microparticles were washed several times with sterile filtered purified water, and freeze-dried to prepare microparticles.

Example 2

Examples 2 was performed in the same manner as in Example 1, except that 5% by weight of mannitol was further mixed based on the total weight % of the second mixture.

Example 3

Example 3 was performed in the same manner as in Example 1, except that the weight ratio of the polylactide-co-glycolide and the deslorelin acetate was 30:1.

Example 4

Example 4 was performed in the same manner as in Example 1, except that the weight ratio of the polylactide-co-glycolide and the deslorelin acetate was 1:1.

Example 5

Example 5 was performed in the same manner as in Example 1, except that the weight ratio of the polylactide-co-glycolide and the deslorelin acetate was 15:1.

Example 6

Example 6 was performed in the same manner as in Example 1, except that the weight ratio of the polylactide-co-glycolide and the deslorelin acetate was 40:1.

Example 7

The Example 7 was performed in the same manner as in Example 1, except that the temperature conditions during stirring were 17° C. for the first stirring, 25° C. for the second stirring, and 40° C. for the third stirring.

Example 8

Example 8 was performed in the same manner as in Example 1, except that 0.5% by weight of polyvinyl alcohol, 5% by weight of mannitol, and the remaining water were mixed to prepare a mixed solution, and the mixed solution was used in a water bath to collect microparticles generated at the cross-point of the flow of the first mixture and the flow of the second mixture.

2. Preparation of Composition for the Subcutaneous Injection

The microparticles prepared in Examples 1 to 8 were added to 2.0 ml of a suspension solvent based on a 3-month amount corresponding to API 26 μm/day, and then uniformly suspended to prepare a composition for subcutaneous injection.

The suspension solvent was composed of the composition shown in Table 1 below.

TABLE 1

| Basis of contents | Purpose of mixing | Ingredient name | Amount | Unit |
|---|---|---|---|---|
| 2.0 mL | Isotonic agent | D-Mannitol | 100.0 | mg |
| | Suspending agent | Sodium carboxymethylcellulose | 10.0 | mg |
| | Suspending agent | Polysorbate 80 | 10.0 | mg |
| | Solvent | Injection water | Remainder | |

Experimental Example 1: Drug Release Experiment of Sustained-Release Microparticles About 100 mg of the microparticles of Examples 1 to 6 were added into a glass test container having 120 mL of an inner volume, and 100 mL of the release test solution was filled. As an accelerated experiment condition for drug release, it was placed in a water bath at 45° C., and was reciprocated with an amplitude of 4 cm and a shaking frequency of 120 times/min to conduct a drug release experiment. Upon a collection of sample, the bottle was shaken and mixed well, and 1 mL was taken therefrom. After centrifugation at 13,000 rpm for 3 minutes, the supernatant was taken and analyzed by high performance liquid chromatography.

The drug release test results are shown in Table 2 below.

TABLE 2

| day | Example 1 | Example 2 | Example 3 | Example 4 | Example 5 | Example 6 |
|---|---|---|---|---|---|---|
| 0 | 0 | 0 | 0 | 0 | 0 | 0 |
| 0.02 | 32.60 | 29.88 | 27.85 | 35.00 | 15.30 | 3.49 |
| 0.04 | 38.83 | 34.63 | 30.73 | 40.3 | 17.32 | 5.53 |
| 0.06 | 44.97 | 41.87 | 39.6 | 47.1 | 20.6 | 6.49 |
| 0.08 | 42.47 | 44.46 | 23.4 | 50.3 | 21.7 | 7.51 |
| 0.10 | 46.80 | 48.80 | 28.80 | 50.40 | 21.90 | 8.70 |
| 0.13 | 50.53 | 48.52 | 32.53 | 53.70 | 23.70 | 9.42 |
| 0.17 | 47.03 | 46.23 | 33.67 | 65.80 | 22.75 | 10.42 |
| 0.25 | 62.60 | 58.61 | 29.53 | 70.60 | 24.64 | 12.24 |
| 0.33 | 50.93 | 56.91 | 29.03 | 76.30 | 25.86 | 12.12 |
| 0.50 | 35.67 | 55.47 | 17.27 | 65.20 | 26.75 | 13.24 |
| 1.00 | 23.32 | 33.40 | 12.38 | 51.80 | 23.46 | 11.05 |
| 7 | 33.25 | 34.27 | 9.13 | 35.70 | 22.45 | 15.64 |
| 14 | 20.51 | 28.10 | 25.73 | 25.73 | 20.71 | 16.50 |
| 21 | 24.01 | 26.46 | 33.63 | 0.00 | 20.66 | 20.21 |
| 28 | 2.78 | 5.78 | 20.03 | 0.00 | 18.21 | 31.62 |
| 35 | 0.00 | 3.45 | 16.50 | 0.00 | 17.55 | 24.34 |
| 42 | 0.00 | 2.25 | 15.80 | 0.00 | 17.21 | 25.71 |
| 49 | 0.00 | 1.51 | 10.47 | 0.00 | 16.43 | 26.46 |
| 56 | 0.00 | 0.00 | 9.51 | 0.00 | 14.59 | 22.43 |
| 63 | 0.00 | 0.00 | 8.71 | 0.00 | 13.84 | 20.87 |
| 70 | 0.00 | 0.00 | 8.59 | 0.00 | 12.54 | 20.67 |
| 77 | 0.00 | 0.00 | 6.53 | 0.00 | 11.62 | 18.51 |
| 84 | 0.00 | 0.00 | 5.49 | 0.00 | 7.53 | 17.05 |
| 91 | 0.00 | 0.00 | 1.54 | 0.00 | 5.19 | 16.59 |

(Unit: ng/ml)

According to Table 2, in the case of Example 4, the drug was released too much at the beginning, and after 14 days, the release is almost completed, so it is difficult to exhibit a long-term drug release effect. In addition, in the case of Example 6, the drug was released too inadequately at the beginning, and the therapeutic effect of the deslorelin drug is insufficient.

On the other hand, in the case of Example 1, it was confirmed that the deslorelin was continuously released for one month. In the case of Example 2, it was confirmed that the drug was prepared in the same ratio of the deslorelin and the biodegradable polymer as in Example 1, but the drug release effect was maintained for a long time.

In the case of Examples 3 and 5, it was confirmed that the deslorelin was continuously released for up to 3 months.

Experiment Example 2. Changes in Properties of Microparticles

In order to confirm the change in the properties of the microparticles depending on the stirring conditions, SEM photographs of the microparticles prepared in the same manner as in Examples 1, 7, and 8 were confirmed.

Experimental results are as shown in FIGS. 1 and 2.

It was confirmed that FIG. 1 is a case where the stirring was performed under the conditions of Example 7, and agglomeration between particles occurred when the stirring was not performed under the condition of 25° C. as in Example 7.

On the other hand, in the case of Example 1, as shown in FIG. 2, it is possible not only to prepare microparticles having an even particle diameter, but also to prepare microparticles that have an even surface and do not cause agglomeration between particles.

In addition, in the case of Example 8, as shown in FIG. 2, it was confirmed that it was possible to prepare microparticles in which no aggregation phenomenon between particles occurred.

Although the preferred embodiments of the present disclosures have been described in detail above, the scope of the present disclosure is not limited thereto, and various modifications and improvements by those skilled in the art using the basic concept of the present invention defined in the following claims also belong to the scope of rights of the present disclosure.

INDUSTRIAL APPLICABILITY

The present disclosure relates to sustained-release microparticles containing deslorelin and a preparation method therefor, and more specifically, to sustained-release microparticles containing deslorelin capable of maintaining a chemical castration effect by continuously releasing the deslorelin for a long time when injected into the body of an animal, and a preparation method therefor.

The invention claimed is:

1. A method for preparing sustained-release microparticles containing deslorelin, the method comprising steps of:

1) preparing a first mixture by mixing an active pharmaceutical ingredient (API) mixture in which deslorelin is dissolved in a first solvent and a biodegradable polymer mixture in which a biodegradable polymer is dissolved in a second solvent;

2) dissolving a surfactant in water to prepare a second mixture;

3) injecting the first mixture of the step 1) into a channel in a linear direction and allowing the first mixture to flow therein;

4) injecting the second mixture of the step 2) into a channel formed on either side or one side so as to form a cross-point with the channel in which the first mixture of the step 3) flows in the linear direction and allowing the second mixture to flow therein, and then crossing the flow in the linear direction with the flow in a lateral direction to prepare microparticles in which deslorelin is evenly distributed;

5) collecting the microparticles generated at the cross-point of the step 4);

6) removing an organic solvent present on the surface of the microparticles collected in the step 5); and 7) washing and drying the microparticles of the step 6), wherein the prepared microparticles are an $O_1$ (Oil)/$O_2$ (Oil)/W (Water) emulsion or a $W_1$ (Water)/O (Oil)/$W_2$ (Water) emulsion, and have an average diameter of 25 to 140 μm.

2. The method of claim 1, wherein the microparticles contain the deslorelin and the biodegradable polymer at a weight ratio of 1:4 to 1:30.

3. The method of claim 1, wherein the API mixture is mixed with the deslorelin and the first solvent at a weight ratio of 1:3 to 1:8.

4. The method of claim 1, wherein the biodegradable polymer mixture is mixed with the biodegradable polymer and the second solvent at a weight ratio of 1:10 to 3:10.

5. The method of claim 1, wherein the first mixture is mixed with the API mixture and the biodegradable polymer mixture at a weight ratio of 1:4 to 1:20.

6. The method of claim 1, wherein the second mixture further comprises an osmotic pressure regulator.

7. The method of claim 1, wherein the solvent is selected from the group consisting of methanol, chloroform, chloromethane, dichloromethane, trichloroethane, water, ethanol, dimethylsulfoxide, and a mixture thereof.

8. The method of claim 1, wherein the biodegradable polymer is selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof.

9. The method of claim 1, wherein the ratio of a width (w) of the cross section of the channel to an average diameter (d') of the microparticles is in the range of 0.7 to 1.3.

10. The method of claim 1, wherein the ratio of a depth (d) of the cross section of the channel to an average diameter (d') of the microparticles is in the range of 0.7 to 1.3.

* * * * *